United States Patent [19]

Frank

[11] 4,196,302
[45] Apr. 1, 1980

[54] QUATERNARY PHOSPHONIUM SALTS BEARING CARBAMATE GROUPS

[75] Inventor: Arlen W. Frank, Slidell, La.

[73] Assignee: The United States of America as represented by the Secretary of Agriculture, Washington, D.C.

[21] Appl. No.: 18,087

[22] Filed: Mar. 6, 1979

Related U.S. Application Data

[62] Division of Ser. No. 964,853, Nov. 29, 1978.

[51] Int. Cl.$^2$ ............... C07C 125/06; C09K 3/28
[52] U.S. Cl. ............................ 560/24; 560/25; 560/115; 560/157; 560/158; 252/8.1; 8/115.5; 8/116 R; 427/223
[58] Field of Search ............... 560/25, 158, 115, 24, 560/157

[56] References Cited

U.S. PATENT DOCUMENTS

| | | | |
|---|---|---|---|
| 2,860,166 | 11/1958 | Newcomer | 560/25 |
| 3,992,430 | 11/1976 | Bacskai | 560/25 |

OTHER PUBLICATIONS

Wagner & Zook, Synthetic Organic Chemistry, John Wiley & Sons, Inc., N.Y., p. 647 (1965).

*Primary Examiner*—Howard T. Mars
*Assistant Examiner*—G. T. Breitenstein
*Attorney, Agent, or Firm*—M. Howard Silverstein; David G. McConnell; Raymond G. Von Bodungen

[57] ABSTRACT

Novel quaternary phosphonium salts, bearing one or more carbamate groups attached through nitrogen, are prepared by condensing a hydroxymethyl phosphonium salt having the formula $[R_{4-n}P(CH_2OH)_n]^+X^-$ with an alkyl carbamate having the formula $NH_2CO_2R'$. The products, which have the general formula $[R_{4-n}P(CH_2NHCO_2R')_n]^+X^-$, are useful as finishing agents for imparting flame retardant or durable press properties to cotton fabrics.

3 Claims, No Drawings

QUATERNARY PHOSPHONIUM SALTS BEARING CARBAMATE GROUPS

CROSS REFERENCE TO RELATED APPLICATION

This is a division of application Ser. No. 964,853 filed Nov. 29, 1978.

BACKGROUND OF THE INVENTION (1) Field of the Invention

This invention relates to novel quaternary phosphonium salts. More particularly, it relates to quaternary phosphonium salts in which one or more of the phosphorus substituents bears a carbamate group attached through its nitrogen atom.

(2) Description of the Prior Art

Heretofore, it was not generally known that quaternary phosphonium salts bearing nitrogen-containing groups are capable of existence, because the amines used in their preparation cause the phosphonium salt to rupture, displacing formaldehyde and a tertiary phosphine. The sole exceptions are the arylaminoalkyl phosphonium salts, described by A. W. Frank and G. L. Drake, Jr., in U.S. Pat. No. 3,987,098 (1976), which retain their quaternary structure by virtue of the weak basicity of the aromatic amines.

SUMMARY OF THE INVENTION

The instant invention relates to novel quaternary phosphonium salts having the general formula $[R_{4-n}P(CH_2NHCO_2R')_n]^+X^-$ where R and R' are radicals selected from the group consisting of alkyl, cycloalkyl and aryl, n is an integer from 1 to 4, and X is an inorganic radical, and processes for preparing a quaternary phosphonium salt bearing at least one carbamate group attached through nitrogen which comprises condensing a hydroxymethyl phosphonium salt having the formula $[R_{4-n}P(CH_2OH)_n]^+X^-$ where R is a radical selected from the group consisting of alkyl, cycloalkyl and aryl, n is an integer from 1 to 4, and X is an inorganic radical, with an alkyl carbamate having the formula $NH_2CO_2R'$, in a molar ratio of at least 1:1 with respect to n, and recovering the product from the resulting reaction mixture.

It is the principal object of the invention to show that stable nitrogen-containing quaternary phosphonium salts of novel structure can be prepared in which the nitrogen is furnished by an alkyl carbamate. The preparation and properties of a variety of such compounds are described, together with methods for their purification, interconversion, and use as flame retardants for cotton.

Other objects of the invention will become obvious from the detailed description of the preferred embodiments of the invention.

DESCRIPTION OF THE PREFERRED EMBODIMENTS

The novel quanternary phosphonium salts of this invention have the general formula $$[R_{4-n}P(CH_2NHCO_2R')_n]^+X^-$$

where R and R' are radicals selected from the group consisting of alkyl, cycloalkyl and aryl, n is an integer from 1 to 4, and X is an inorganic radical.

In accordance with the practice of this invention, the new compounds are prepared by condensing a hydroxymethyl phosphonium salt having the general formula $$[R_{4-n}P(CH_2OH)_n]^+X^-$$

where R, n and X are as defined above, with an alkyl carbamate having the general formula $NH_2CO_2R'$, where R' is as defined above, in a ratio of at least 1:1 with respect to n, and recovering the product from the resulting reaction mixture. This condensation is embodied in the following equation:

$$[R_{4-n}P(CH_2OH)_n]^+X^- + nNH_2CO_2R' \rightarrow [R_{4-n}P(CH_2NHCO_2R')_n]^+X^- + nH_2O$$

The hydroxymethyl phosphonium salts employed in the practice of this invention are exemplified by (hydroxymethyl)-triphenylphosphonium chloride, tetrakis(hydroxymethyl)phosphonium chloride (THPC), tetrakis(hydroxymethyl)phosphonium iodide, octakis(hydroxymethyl)diphosphonium sulfate (THPS), and the like.

The alkyl carbamates employed in the practice of this invention are exemplified by methyl carbamate, ethyl carbamate, isopropyl carbamate, 2-methoxyethyl carbamate, n-butyl carbamate, and the like.

The condensation between the hydroxymethyl phosphonium salt and the alkyl carbamate is carried out at temperatures ranging from 75° C. to 150° C., preferably in the presence of a solvent such as toluene, xylene, butanol or water. For small scale work, it is convenient to employ a solvent such as toluene or xylene and to remove the water, as it is formed, by azeotropic distillation; the progress of the reaction, and the extent of its completion, is thereby easily determined. For large scale work, it is more convenient to omit the solvent, using only the water present in the technical reagent coupled with that generated during the condensation.

The relative proportion of the reactants may be varied at will. Preferably, one mole of the alkyl carbamates is employed per hydroxyl group in the hydroxymethyl phosphonium salt, but an excess of one reactant or the other may be employed if it is deemed necessary to drive the reaction to completion.

The condensation is usually carried out at atmospheric pressure, but may also be carried out at higher or lower pressures.

Quaternary phosphonium salts are known in which one or more of the phosphorus substituents bears a carbamate group attached through one of its oxygen atoms, rather than its nitrogen atom. Such compounds, which have the general formula $$[R_{4-n}P(CH_2O_2CNHR')_n]^+X^-$$

where R, R', n and X have the same meaning as above, are isomers of the products of this invention, having the same molecular formulas but different structures and different physical and chemical properties. Such isomeric products are described by R. A. Askarova et al, Zh. Obshch. Khim. 44, 1438 (1974) for the compound R'=C_6H_5, n=4, X=C, and by H. Hellman et al, Justus Liebigs Ann. Chem. 659, 49 (1962) for the compound R=R'=C_6H_5, n=1, X=BF_4. In both cases, the method of preparation was the addition of phenyl isocyanate to the appropriate hydroxymethyl phosphonium salt, a method distinctly different from the method employed in the practice of this invention.

The novel compounds of this invention are useful as plasticizers, lubricant additives, and surface-active agents. They are particularly useful as finishing agents for cotton, imparting flame retardant or durable-press properties to cotton or cotton blend textile fabrics.

The following examples are given to illustrate the preparation and properties of the novel compounds of this invention, and their use as flame retardants for cotton. The examples are given merely for purposes of illustration, and should not be construed as limiting the scope of the invention. The flammability of the treated fabrics was determined by the Match Test, as described by W. A. Reeves and G. L. Drake, Jr., "Flame Resistant Cotton", Merrow, Watford Herts., England, 1971, p. 14. Wrinkle recovery was determined by the Monsanto Test, as described in the "Annual Book of ASTM Standards", American Society for Testing and Materials, Philadelphia, Pa., 1974, Part 32, p. 226.

EXAMPLE 1

This example illustrates the preparation of tetrakis(N-carbomethoxylaminomethyl)phosphonium chloride, hereinafter referred to as TMPC.

A mixture of 47.64 g (0.25 mol) of THPC, 75.07 g (1.00 mol) of methyl carbamate and 200 ml of toluene was heated to reflux in an apparatus fitted with a Dean-Stark trap for azeotropic removal of the water. The mixture was held at reflux until the evolution of water ceased; after 2.5 hr, 18.5 ml (1.03 mol) had been collected. The product crystallized on standing to a hard mass and was broken up, triturated under ethyl acetate, filtered, and dried, giving 90.67 g (86.5% yield) of $(CH_3O_2CNHCH_2)_4P^+Cl^-$(TMPC), mp 177° C. d. Two recrystallizations from ethanol afforded pure TMPC as a white, crystalline solid, mp 189° C. d. IR (Nujol) 770m, 787w, 850m, 855m,sh, 865m, 966w, 1005m, 1020m, 1160m, 1265vs, 1300s, 1540vs (NH, amide II), 1700s and 1740vs (C=O, amide I; doublet in Nujol but a singlet, 1730vs, in DMSO), 3220m (NH bonded), and 3300m (NH free) $cm^{-1}$. $^1H$ NMR (DMSO-$d_6$) δ 3.63 (s, 12H, $CH_3$), 4.32 (t, 8H, $CH_2$, J=5.0 Hz, collapsing with $D_2O$ to d, J=4.0 Hz), and 8.05 (m, ~4H, NH, vanishing with $D_2O$). $-P$ NMR (DMSO) δ−30.7.

Anal. Calcd for $C_{12}H_{24}ClN_4O_8P$: C, 34.41; H, 5.78; Cl, 8.47; N, 13.38; P, 7.40; mol. wt., 419. Found: C, 34.64; H, 5.66; Cl, 8.71; N, 13.24; P, 7.53; mol. wt. (osmometric in $H_2O$), 249, 259.

TMPC is partially soluble in water, DMSO (7 ml/g) and methanol, and insoluble in other common organic solvents. Its aqueous solution is mildly acidic (pH 4.5). It can be recrystallized from ethanol (20 ml/g) or 2-propanol (75 ml/g), and is air stable, nonhygroscopic and odorless.

EXAMPLE 2

A 5 liter flask was charged with 1191 g (5 mol) of 80% aqueous THPC and 750 g (10 mol) of methyl carbamate, heated briefly to 100° C., allowed to cool to 65° C., charged with another 750 g of methyl carbamate, and heated at gentle reflux (110° C.) for 3 hr. Next day, the crystalline mass was broken up, triturated in portions with ethanol in evaporating dishes. The product, TMPC, was a white, crystalline solid, 1472 g, mp 189° C. d (70.3% yield). Workup of the mother liquor raised the yield to 80.1%.

EXAMPLE 3

Reaction of THPC (47.64 g, 0.25 mol) with 89.10 g (1.00 mol) of ethyl carbamate [Caution: carcinogenic], following Example 1, gave 71.53 g (60.2% yield) of tetrakis(N-carbethoxylaminomethyl)phosphonium chloride, $(C_2H_5O_2CNHCH_2)_4P^+$ $Cl^-$, as a white, crystalline solid, mp 112°–113° C., after two recrystallizations from ethyl acetate. IR (Nujol) 772w, 782w, 850w, 860w, 1020m, 1085w, 1145m, 1170m, 1215m, 1230m,sh, 1260vs, 1280s, 1300s, 1515vs and 1535s (NH, amide II), 1680s and 1730s (C=O, amide I; doublet in Nujol or conc. KBr, changing to singlet in $CHCl_3$ or dil. KBr), 3230m (NH bonded), and 3360 w (NH free) $cm^{-1}$. $^1H$ NMR ($CDCl_3$) δ 1.26 (t, 12H, $CH_3$, J=7.0 Hz) 4.17 (q, $CH_2C$, J=7.0 Hz), 4.42 (m, $PCH_2$, collapsing with $D_2O$ to d, δ 4.46, J=3.0 Hz; total $CH_2$, 16H), and 7.43 (m, NH, vanishing with $D_2O$). $-P$ NMR (DMSO) δ −31.2.

Anal. Calcd. for $C_{16}H_{32}ClN_4O_8P$: C, 40.46; H, 6.79; Cl, 7.47; N, 11.80; P, 6.52. Found: C, 40.49; H, 6.80; Cl, 7.59; N, 11.60; P, 6.61.

The product is soluble in water, ethanol, chloroform, benzene, DMSO (1.5 ml/g) and acetone, and insoluble in ether, carbon tetrachloride and cyclohexane. Its aqueous solution is mildly acidic. It is readily recrystallized from ethyl acetate (5 ml/g), but tends to oil out from hot carbon tetrachloride or toluene.

EXAMPLE 4

The NH hydrogens in the product of Example 3 were exchanged for deuterium by dissolving the compound in $D_2O$, stripping in a rotary evaporator, and drying in a vacuum desiccator. This sequence was repeated twice. The free and H-bonded NH bands in the IR spectrum were shifted from 3360 and 3230 $cm^{-1}$ to 2500 and 2370 $cm^{-1}$, respectively, and the amide II doublet was shifted from 1515 and 1535 $cm^{-1}$ to - (Nujol-masked) and 1425 $cm^{-1}$.

EXAMPLE 5

Reaction of 9.53 g (0.05 mol) of THPC with 20.62 g (0.20 mol) of isopropyl carbamate, following Example 1 but using ether instead of ethyl acetate, gave 9.32 g (45.6% yield) of tetrakis(N-carbisopropoxylaminomethyl)phosphonium chloride, $[(CH_3)_2CHO_2CNHCH_2]_4P^+$ $Cl^-$, as a white, crystalline solid, mp 140°–41° C., after two recrystallizations from water. IR (Nujol) 772w, 832w, 875w, 884w, 925w, 934w, 1005m, 1015m, 1110s, 1145m, 1175m, 1250vs, 1280m, 1300m, 1510s (NH, amide II), 1720s and 1730vs (C=O, amide I), 3220m (NH bonded), and 3320m (NH free) $cm^{-1}$. $^1H$ NMR ($CDCl_3$) δ 1.27 (d, 24H, $CH_3$, J=6.0 Hz), 4.44 (br s, $CH_2$, resolved with $D_2O$ to d, δ 4.46, J=3.0 Hz), 4.94 (m, CH, J=6.0 Hz; combined $CH_2$ and CH, 12H), and 7.31 (m, 4H, NH, vanishing with $D_2O$).

Anal. Calcd. for $C_{20}H_{40}ClN_4O_8P$: C, 45.24; H, 7.59; Cl, 6.68; N, 10.55; P, 5.83. Found: C, 45.11; H, 7.37; Cl, 6.63; N, 10.74; P, 5.94.

The product is soluble in ethanol, chloroform, carbon tetrachloride and benzene, and insoluble in ether. It can be recrystallized from ethyl acetate (10 ml/g) or water (3 ml/g).

EXAMPLE 6

Fifty grams of Bio-Rad AG 50W-X4, a high porosity nuclear sulfonic acid cation exchange resin suitable for organic ions of mol wt 300–400 or over, was charged into a 19×600 mm chromatographic column with a sealed-in coarse fritted disk, backwashed thoroughly with water, and rinsed with water until the effluent was neutral and chloride-free. A solution of 4.19 g (10.0 mmol) of TMPC in 30 ml of warm water was transferred to the column and eluted with water, collecting the effluent in 50 ml fractions at a flow rate of 30 drops/min. The top 2 in. of the resin lightened noticeably. Titration of the first five effluent fractions with 0.1 N NaOH gave 2.42, 7.32, 0.04, 0.02 and 0.01 mmol of HCl for a total of 9.82 mmol (98.2% yield). The resin was then eluted with 6 N HCl at the same flow rate, causing the resin to contract from 12 to 8.5 in., and restoring its original color. The effluent, collected in 50 ml fractions and stripped carefully in a rotary evaporator at 50° C./3 mm, yielded 0, 2.26, 1.31, 0.57 and 0.31 g of crystalline TMPC, totaling 4.45 g (106.2% yield) with mp's decreasing progressively from 177.5° C. d. to 165° C. d. The four fractions, combined and recrystallized from ethanol, yielded 3.25 g (77.5% yield) of pure TMPC, mp 189° C. d.

EXAMPLE 7

Reaction of 9.53 g (0.05 mol) of THPC with 29.29 g (0.25 mol) of n-butyl carbamate, following Example 1, gave 37.67 g of a colorless oil that partly crystallized on standing. Attempts to separate the excess n-butyl carbamate from the product by extraction with hot ligroin, ether or carbon tetrachloride were unsuccessful, for the two substances exhibit the same solubility behavior. Half of the mixture was therefore dissolved in ethanol (25 ml) and percolated through the ion exchange resin described in Example 6, using ethanol as the eluent. The neutral fractions yielded 17.6 mmol (70.4% yield) of HCl, 3.10 g (21.2% recovery) of n-butyl carbamate, and 2.24 g (14.6% yield) of di-n-butyl N,N'-methylenedicarbamate, mp 93°–95° C. (identified by comparison of its IR, NMR and mp with an authentic sample, mp 97°–98° C.). The phosphonium salt fractions, eluted with ethanolic HCl, yielded 7.83 g of a viscous, colorless oil, $n_D^{20}$ 1.4839, whose composition, determined by NMR and elemental analysis, comprised some unreacted THPC (11.2% yield) in addition to the product (38.4% yield). To remove the unreacted THPC, the oil was taken up in chloroform (50 ml), extracted twice with water, filtered, stripped and dried, giving 4.71 g (30.1% yield) of tetrakis(N-carbo-n-butoxylaminomethyl)phosphonium chloride, $(C_4H_9O_2CNHCH_2)_4P^+Cl^-$, as a viscous, colorless oil, $n_D^{20}$ 1.4951. IR (Nujol) 1515vs (NH, amide II), 1710vs (C=O, amide I) and 3230s (NH) cm$^{-1}$. $^1$H NMR (CDCl$_3$) δ 0.94 (t, 12H, CH$_3$, J=6.0 Hz), 1.1–2.0 (m, 16H, CH$_2$C), 4.13 (t, 8H, OCH$_2$, J=6.0 Hz), 4.43 (m, 8H, PCH$_2$) and 7.37 (m, 4H, NH, vanishing slowly with D$_2$O). $^{31}$P NMR (CHCl$_3$) δ −30.0.

The product is soluble in all of the common organic solvents, including toluene and hot ligroin, and insoluble in water.

EXAMPLE 8

Reaction of 9.53 g (0.05 mol) of THPC with 35.74 g (0.30 mol) of 2-methoxyethyl carbamate, following Example 1, gave 40.71 g of a viscous, almost colorless oil that resisted efforts at crystallization or conversion to a crystalline oxalate or picrate. Half of the oil was therefore dissolved in 10 ml of water and percolated through the ion exchange resin described in Example 6, using water as the eluent. The neutral fractions yielded 16.9 mmol (67.6% yield) of HCl. The phosphonium salt fractions yielded 11.10 g of oil which was taken up in chloroform, filtered, stripped and dried (omitting the extraction with water, since the partition is unfavorable), giving 9.05 g (53.7% yield) of tetrakis[N-carbo(2-methoxyethoxyl)aminomethyl]phosphonium chloride, $(CH_3OCH_2CH_2O_2CNHCH_2)_4P^+Cl^-$, as a viscous, colorless oil, $n_D$ 1.5094. IR (neat) 1515s (NH, amide II), 1720vs (C=O, amide I) and 3240m (NH) cm$^{-1}$. $^1$H NMR (CDCl$_3$) δ 3.38 (s, 12H, CH$_3$), 3.61 (m, 8H, 2-CH$_2$), 4.29 (m, 8H, 1-CH$_2$), 4.53 (m, 8H, PCH$_2$), and 7.42 (m, ~4H, NH, vanishing slowly with D$_2$O). $^{31}$P NMR (CHCl$_3$) δ −31.0.

The phosphonium salt is soluble in water, ethanol, acetone, chloroform, ethyl acetate and hot toluene.

EXAMPLE 9

Reaction of 3.29 g (0.01 mol) of (hydroxymethyl)triphenylphosphonium chloride with 0.75 g (0.01 mol) of methyl carbamate, following Example 1 but using benzene instead of ethyl acetate, gave 2.82 g (73.1% yield) of (N-carbomethoxylaminomethyl)triphenylphosphonium chloride, $(CH_3O_2CNHCH_2)(C_6H_5)_3P^+Cl^-$, as a white, crystalline solid, mp 198.5°–199° C. d after recrystallization from 2-propanol. IR (Nujol) 688m, 697w, 720m, 736m, 752m, 774w, 841w, 994w (P—C$_6$H$_5$), 1020m, 1110s, 1165w, 1190m, 1255vs, 1310m, 1430s (P—C$_6$H$_5$), 1460m, 1540m (NH, amide II), 1580w (C=C), 1720vs (C=O, amide I), and 3170m,sh (NH) cm$^{-1}$. $^1$H NMR (DMSO-d$_6$) δ 2.36 (s, 3H, CH$_3$), 4.39 d pair, 2H, CH$_2$, J=3.0 Hz, collapsing with D$_2$O to d, δ 4.31, J$_{PCH}$=3.0 Hz), 6.87 (m, 15H, C$_6$H$_5$; d at δ 6.92, J=2.0 Hz collapsing with D$_2$O to s, δ 6.90) and 7.67 (m, 1H, NH, vanishing with D$_2$O). −P NMR (CHCl$_3$) δ −20.0.

Anal. Calcd for C$_{21}$H$_{21}$ClNO$_2$P: C, 65.37; H, 5.49; Cl, 9.19; N, 3.63; P, 8.03. Found: C, 65.04; H, 5.67; Cl, 9.35; N, 3.47; P, 8.07.

The phosphonium salt is soluble in water, ethanol, and chloroform, and insoluble in ether, carbon tetrachloride, acetone and ethyl acetate. It can be recrystallized from 2-propanol (5 ml/g).

EXAMPLE 10

A mixture of 270.8 g (0.5 mol) of 75% THPS and 300.2 g (4.0 mol) of methyl carbamate was heated to reflux with constant stirring, held at 100° to 108° C. for 2 hr, allowed to cool, and then stripped of water under reduced pressure, giving 443.8 g (102.9% yield) of octakis(N-carbomethoxylaminomethyl)-diphosphonium sulfate, $[(CH_3O_2CNHCH_2)_4P]_2^{++}SO_4^{--}$, as an almost colorless, tacky glass. IR (KBr) 1720vs (C=O, amide I), 1515vs (NH, amide II) and 3300s (NH) cm$^{-1}$. $^{31}$P NMR (H$_2$O) δ −28.8.

EXAMPLE 11

A solution of 2.08 g (0.01 mol) of barium chloride in 25 ml of water was mixed with a solution of 8.88 g (0.01 mol) of the product of Example 10 in 25 ml of water, causing an immediate separation of solids. The mixture was heated to boiling to coagulate the solids, allowed to cool and filtered, giving 2.31 g (99.0% yield) of barium sulfate. The filtrate, stripped under vacuum, left a crystalline residue which was rinsed with ethanol, giving 5.62 g (67.1% yield) of TMPC, mp 187.5°–188° C. d, identical to the product of Example 1.

EXAMPLE 12

TMPC (8.38 g, 0.02 mol) was added to a solution of sodium iodide (3.00 g, 0.02 mol) in 30 ml of ethanol, heated at reflux for 1 hr, cooled, and filtered, giving 3.23 g of granular solid consisting of sodium chloride and unreacted TMPC. The latter was removed by stirring with DMSO, leaving 0.67 g (57.3% yield) of sodium chloride. The ethanol filtrate was stripped, taken up in hot chloroform, filtered to remove unreacted sodium iodide (0.22 g, giving a positive test with acidified iodate), and stripped again. The residue (8.45 g) was recrystallized from ethanol, giving 5.01 g (49.1% yield) of tetrakis(N-carbomethylaminomethyl)phosphonium iodide, $(CH_3O_2CNHCH_2)_4P^+I^-$, as a white, crystalline solid, mp 142.5°–143° C. IR (Nujol) 768m, 784w, 848m, 860m, 963w, 1005m, 1020m, 1150m, 1185m,br, 1205m, 1260vs, 1295s, 1535vs (NH, amide II), 1690s and 1730vs (C=O, amide I), 3230m (NH, bonded) and 3300m,sh (NH free) cm$^{-1}$. $^1$H NMR (DMSO—d$_6$) δ 3.67 (s, 12H, CH$_3$), 4.33 (t, 8H, CH$_2$, J=5.0 Hz, collapsing with D$_2$O to d, J=4.0 Hz), and 7.67 (m, 4H, NH, vanishing with D$_2$O). $^{31}$P NMR (DMSO) δ −30.3.

Anal. Calcd. for $C_{12}H_{24}IN_4O_8P$: I, 24.87; P, 6.07. Found: I, 24.50 (gravimetric), 25.05 (by iodometric titration); P, 6.12.

EXAMPLE 13

A solution of 8.38 g (0.02 mol) of TMPC in 200 ml of methanol was percolated through the ion exchange resin described in Example 6. It was necessary to wrap the column in heating tape and warm it to 40°–50° C. to prevent the salts from crystallizing. The column was eluted with hydrogen bromide in methanol, yielding four liquid fractions (6.79 g) followed by eight solid fractions (19.19 g). The solids were combined, shaken with ethanol, and filtered, giving 6.50 g (70.2% yield) of tetrakis(N-carbomethoxylaminomethyl)phosphonium bromide, $(CH_3O_2CNHCH_2)_4P^+Br^-$, mp 180°–184° C. d. One recrystallization from ethanol (75 ml/g) afforded the pure salt as a white, crystalline solid, mp 185°–186° C. d, suffering no loss in weight when heated in a drying pistol for 2 hr at 100° C./0.5 mm. IR (Nujol) 770m, 786w, 847m, 863m, 965w, 1005m, 1020m, 1160m, 1185m, 1210m, 1235s,sh, 1260vs, 1300s, 1370m, 1550vs (NH, amide II), 1700s and 1730vs (C=O, amide I), 3220s (NH bonded) and 3320m (NH free) cm$^{-1}$. $^1$H NMR (DMSO—d$_6$) δ 3.65 (s, 12H, CH$_3$), 4.35 (t, 8H, CH$_2$, J=5.0 Hz, collapsing with D$_2$O to d, J=4.0 Hz), and 7.75 (br t, 4H, NH, vanishing with D$_2$O). $^{31}$P NMR (DMSO) δ −30.0.

Anal. Calcd for $C_{12}H_{24}BrN_4O_8P$: Br, 17.25; P, 6.69. Found: Br, 17.71; P, 6.93.

EXAMPLES 14 TO 17

These examples illustrate the application of TMPC to cotton fabric without the use of a binding agent.

An 80×80 desized, scoured and bleached cotton printcloth was cut into 12"×24" swatches, immersed in a warm solution of 35.2 g (84 mmol) of TMPC, 5.1 g (25 mmol) of magnesium chloride hexahydrate, and 0.2 g of Triton X-100 (a wetting agent) in 59.5 g of water, padded to about a 95% wet pickup, and dried at 85° C. for 4 min. in a forced draft oven. The swatches were then cured for 4 min. at temperatures ranging from 160° C. to 220° C., rinsed 15 min. in hot running tap water, and line-dried. The results are assembled in Table I.

Table I

| Example | Cure Temp., °C. | % Add-on Unrinsed | % Add-on Rinsed | Match Angle Unrinsed | Match Angle Rinsed |
|---|---|---|---|---|---|
| 14 | 160 | 24.2 | 0 | 100 | 0 |
| 15 | 180 | 22.3 | −0.4 | 100 | 0 |
| 16 | 200 | 10.4 | −0.6 | 90 | 0 |
| 17 | 220 | 8.3 | −0.8 | 80 | 0 |

The TMPC was not bound to the cotton, but did impart some flame retardance, evidenced by the match test angle, before rinsing. The swatches cured at 180° C. or above were discolored but not badly tendered.

EXAMPLE 18

This example illustrates the preparation of a methylol derivative of one of the products of this invention, TMPC.

A mixture of 4.19 g (0.01 mol) of TMPC, 3.24 g (0.04 mol) of 37% formalin solution and 1.00 g (0.01 mol) of conc. HCl was heated at reflux for 1 hr, cooled and stripped under vacuum, giving 5.04 g (93.5% yield) of the tetramethylol derivative of TMPC as a glassy powder. The product was soluble in water, acetone and acetonitrile, and insoluble in ether, chloroform and benzene. Its IR spectrum showed a strong OH peak at 3400 cm$^{-1}$, and the amide II NH peak at 1540 cm$^{-1}$ in TMPC had almost vanished.

No TMPC was regenerated when the product was dissolved in ethanol, nor when it was dissolved in water and neutralized with sodium bicarbonate. In contrast, TMPC was recovered unchanged when the HCl was omitted, or when the solvent was methanol instead of water.

The dimethylol derivative of TMPC was prepared in a similar manner, using half as much formalin. The product, a colorless oil (98.1% yield), showed a strong OH peak in its IR spectrum at 3400 cm$^{-1}$, and an amide II NH peak at 1530 cm$^{-1}$ that had about half of its intensity in TMPC.

EXAMPLES 19 TO 24

These examples illustrate the application of TMPC to cotton fabric with formaldehyde as the binding agent.

An 80×80 desized, scoured and bleached cotton printcloth was cut into 12"×24" swatches, immersed in 50.0 g of a solution containing 22.6 g (42 mmol) of the tetramethylol derivative of TMPC—prepared as described in Example 18—, 12.5 mmol of a catalyst, and 0.1 g of Triton X-100, padded to about a 95% wet pickup, dried at 85° C. for 4 min. in a forced-draft oven and cured at 160° C. for 4 min. in another forced-draft oven. The swatches were then rinsed 15 min. in hot running tap water and line-dried. The results of a series of such experiments with different catalysts are assembled in Table II.

Table II

| Example | Catalyst | pH | % Add-on | % P | % N | WRA (W + F) |
|---|---|---|---|---|---|---|
| 19 | (HOCH$_2$CH$_2$)$_3$N . HCl | 3.2 | 6.9 | 0.48 | 0.78 | 265 |
| 20 | HCl | 0.8 | 6.2 | 0.53 | 0.83 | 274 |
| 21 | MgCl$_2$/citric acid | 2.8 | 7.6 | 0.49 | 0.78 | 272 |
| 22 | None | 3.7 | 5.0 | 0.46 | 0.67 | 261 |
| 23 | NH$_4$Cl | 3.8 | 4.5 | 0.31 | 0.51 | 223 |
| 24 | Na$_2$CO$_3$ | 8.5 | 0.8 | 0.22 | 0.19 | 180 |

The add-ons were low, compared to 30–35% before rinsing, but the fabrics exhibited good resistance to creasing, with wrinkle recovery angles (conditioned) ranging from 261° to 274°, depending on the acidity of the catalyst. All but the last were slightly discolored. The alkaline catalyst, sodium carbonate, rendered the finish ineffective (example 24).

EXAMPLES 25 AND 26

These examples illustrate the application of TMPC to cotton fabric with dimethylolurea as the binding agent.

An 80×80 desized, scoured and bleached cotton printcloth was cut into 6"×12" swatches, immersed in 50.0 g of a warm solution containing 17.6 g (42 mmol) of TMPC, 10.1 g (84 mmol) of dimethylolurea, and 0.1 g of Triton X-100, padded to about a 95% wet pickup, dried at 85° C. for 4 min. in a forced-draft oven, and cured at 160° C. for 4 min. in another forced-draft oven, rinsed 15 min. in hot running tap water, and line-dried. The process was repeated with half of the reagent strengths for Example 26. The results are assembled in Table III.

Table III

| Example | % Add-on | % P | % N | Match Angle |
|---------|----------|------|------|-------------|
| 25 | 25.6 | 0.76 | 5.02 | 120 |
| 26 | 13.0 | 0.36 | 2.62 | 90 |

A moderate degree of flame retardance was imparted by this treatment, especially at the higher concentration.

I claim:

1. A process for preparing a quaternary phosphonium salt bearing at least one carbamate group attached through nitrogen, which comprises condensing a hydroxymethyl phosphonium salt having the formula

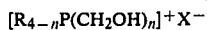

$$[R_{4-n}P(CH_2OH)_n]^+ X^-$$

where R is a radical selected from the group consisting of alkyl, cycloalkyl and aryl, n is an integer from 1 to 4, and X is an inorganic radical, with an alkyl carbamate having the formula $NH_2CO_2R'$, in a molar ratio of at least 1:1 with respect to n, at a temperature of 75° C. to 150° C. and a pressure of about atmospheric, and recovering the product from the resulting reaction mixture.

2. A process in accordance with claim 1 wherein n is 4.

3. A process in accordance with claim 1 wherein X is a radical selected from the group consisting of chloride, bromide, iodide, and sulfate.

* * * * *